United States Patent [19]
Mai et al.

[11] Patent Number: 5,900,239
[45] Date of Patent: May 4, 1999

[54] HAIR GROWTH STIMULATING COMPOSITION CONTAINING TRIGONELLINE OR TRIGONELLIC ACID AND GINSENG

[76] Inventors: Jutta Mai; Heinz Mai, both of Farbrikstr. 16, 78224 Singen/Bohlingen, Germany

[21] Appl. No.: 08/541,421

[22] Filed: Oct. 10, 1995

[51] Int. Cl.$^6$ ..................................................... A01N 65/00
[52] U.S. Cl. ..................... 424/195.1; 132/202; 424/70.1; 514/880; 514/356
[58] Field of Search .................................... 424/195.1, 61, 424/70.1; 514/880, 356; 132/202

[56] References Cited

U.S. PATENT DOCUMENTS 5,567,424  10/1996  Hastings ................................ 424/195.1

OTHER PUBLICATIONS

Chem. Abstrs., vol. 114, No. 24, Jun. 17, 1991, p. 392, column 2, the abstract No. 234872k, Erwin Stuckler, 'Compositions comprising trigonelline and vitamin B6 for hair, nail, and skin care.' DE 4,012,148.

Chem. Abstrs., vol. 113, No. 14, Oct. 1, 1990, p. 360, column 1, the abstract No. 120779j, J. Mai, 'Oral hair growth stimulant based on fenugreek extract.' DD 273,379.

Chem. Abstrs., vol. 110, No. 14, Apr. 3, 1989, p. 413, column 2, the abstract No. 121021f, J. Mai, 'Hair growth agents containing trigonellin or trigonellic acid.' EP 289,639.

Curri et al., Fitoterapia (1986), 57(4), 217–22.

*Primary Examiner*—Irene Marx
*Attorney, Agent, or Firm*—Bachman & LaPointe, P.C.

[57] ABSTRACT

A strengthening agent for living creatures for the care of the skin and horny structures, in particular nails, hooves and claws, and for the stimulating and/or revitalizing of the growth of epidermal structures, in particular hair, this agent containing the alkaloid trigonelline or trigonellic acid, being obtained preferably from an extract of the seeds of a plant from the genus trigonella, in particular fenugreek (*Trigonella foenum* graecum), and being taken orally, characterized by the fact that the agent contains biotin, preferably 5 mg to 10 mg.

5 Claims, No Drawings

HAIR GROWTH STIMULATING COMPOSITION CONTAINING TRIGONELLINE OR TRIGONELLIC ACID AND GINSENG

The present invention relates to a strengthening agent for living creatures for the care of the skin and horny structures, in particular nails, hooves, claws, and for stimulating and reviving growth of epidermal structures, in particular hair, this agent containing the alkaloid trigonelline or trigonellic acid and being obtained, preferably, from an extract of the seeds of a plant from the genus trigonella, particularly fenugreek (*Trigonella phoenum* graecum), and being taken orally.

In the past, a large number of hair-growth agents have been developed, tested, and brought onto the market. Unfortunately, none of these agents has the desired effect, or else it has considerable undesired side effects.

The thinning-out or receding of the growth of hair is generally due to too excessive tightening of the scalp, as a result of which flow of blood to the hair follicles is interrupted or prevented. The reduced supply of nutrients and oxygen to the hair follicles has an unfavorable influence on the production of the protein keratin which is essentially responsible for the growth of hair.

Hair, to be sure, is only a filamentary epidermal structure in man, animals and plants, so that, in particular, a strengthening agent should also serve for the care of the skin. The skin is today exposed to substantially more injurious environmental influences than was the case only a few years ago. Therefore, skin diseases are today increasing to a frightening extent, so that substantially more attention must be paid to the care of the skin in the future.

Horny structures, in particular nails, are also frequently indicators of health. For instance, in the case of certain skin diseases, extensive changes in the nails (onychopathies) occur, in which the nail plate appears rough, furrowed, thickened or raised. Disturbances in the nutrition of the nail, for instance in the case of nervous disorders, can frequently also be noted on the nail itself.

From EP-A 0 289 639, an agent for revivifying and stimulating and strengthening the growth of hair on living creatures is known which contains the alkaloid trigonelline, or trigonellic acid. Although this agent has a very favorable effect on the stimulating and strengthening of the growth of hair, the object of the present invention is further to improve this agent and broaden its field of use.

In order to achieve this object, the agent contains biotin, preferably 5 mg to 10 mg.

Biotin is also known as Vitamin H and is bound by lysine to enzymes and participates as coenzyme in carboxylases in the addition of $CO_2$ (activated carbon dioxide). Biotin-containing enzymes have key functions in glyconeogenesis, in the breaking down of four essential amino acids, and in fatty acid biosynthesis.

Normally, biotin is ingested in the food. In this connection, the amount of biotin taken in the food varies within wide limits and amounts, in the case of average eating habits, to 50 $\mu$g to 100 $\mu$g a day. In accordance with the present invention, it has, however, been found that, with a controlled administration of 5 mg to 10 mg of biotin together with an extract of the seed of fenugreek, an extremely good effect is exerted on the skin, and the growth of hair is stimulated or regenerated. In particular, however, it is also found that disagreeable skin body odors which at times occur are no longer present when fenugreek seeds are taken alone.

A second possibility for improving the agent indicated in EP-A 0 289 639 provides that the agent contains, in addition to trigonelline, an extract of ginseng, preferably 1 g to 2 g. Of course, a combination of the administration of ginseng extract and biotin is also possible.

It is known that a ginseng extract is prepared from the dried main, secondary and hair roots of *Panax ginseng*. It is also known that this extract is a strengthening and toning tonic in conditions of tiredness and weakness, decreased vitality and concentration, as well as in convalescence. However, it has been found by the present invention that the ginseng extract acts almost as accelerator for the action of the alkaloid trigonelline on the stimulation and revivification of the growth of hair. While the positive effects of trigonelline occur after about three to four months, an improvement in the growth of hair can be noted already at the end of one month when ginseng extract it administered. The same is true also when an extract from the seeds of the horse chestnut, preferably 1 g to 2 g, are added to the agent.

Finally, a combination of trigonelline and tocopherol has an excellent effect of the care of the skin and the stimulation and revivification of the hair. The tocopherols are also known under the name Vitamin E, all of them having in their molecule a ring system (chroman ring) having a free or esterified OH group as well as a saturated isoprenoid side chain (16 C atoms).

Up to now, it is has merely been known that, in the case of Vitamin E deficiency, various deficiency symptoms appear with respect to muscle metabolism, membrane function, and the nervous system as a result of the accumulation of radicals and lipid peroxidation. An extremely positive effect on the care of the skin and the growth of hair is, however, obtained in combination with the alkaloid trigonelline.

We claim:

1. A composition for the stimulation of hair growth, comprising:

an amount of an alkaloid selected from the group consisting of trigonelline and trigonellic acid effective for the stimulation of hair growth;

a ginseng extract in an amount of 1 to 2 grams; and at least one material selected from the group consisting of 5 to 10 mg biotin, 1 to 2 grams of a horse chestnut seed extract and 10 to 20 mg of tocopherol.

2. A composition according to claim 1, wherein said composition is in a form suitable for being taken orally.

3. A composition according to claim 1, wherein said composition contains biotin in an amount from 5 to 10 mg.

4. A composition according to claim 1, wherein said composition contains an extract from the seed of the horse chestnut in an amount from 1 to 2 grams.

5. A composition according to claim 1, wherein said composition contains tocopherol in an amount from 10 to 20 mg.

* * * * *